United States Patent [19]

Koyano et al.

[11] 4,444,197

[45] Apr. 24, 1984

[54] ULTRASONIC DIAGNOSTIC PROBE SCANNER

[75] Inventors: Akira Koyano; Seiichiro Mizuno, both of Tokyo, Japan

[73] Assignee: Aloka Co., Ltd., Tokyo, Japan

[21] Appl. No.: 361,762

[22] Filed: Mar. 25, 1982

[30] Foreign Application Priority Data

Mar. 26, 1981 [JP] Japan ................................ 56-43175

[51] Int. Cl.³ ............................................ A61B 10/00
[52] U.S. Cl. ..................................... 128/660; 73/620
[58] Field of Search ............................... 128/660–661, 128/663; 73/618–626

[56] References Cited

U.S. PATENT DOCUMENTS 4,058,001 11/1977 Waxman ............................. 128/660

4,291,578 9/1981 Hetz et al. ....................... 128/660 X

Primary Examiner—Kyle L. Howell
Assistant Examiner—Francis J. Jaworski
Attorney, Agent, or Firm—Koda and Androlia

[57] ABSTRACT

An ultrasonic diagnostic probe scanner for an ultrasonic diagnostic apparatus. The scanner includes a scanner system having six joints, each of which can be rotated within a predetermined plane. The scanner system is supported on a scanner base at one end and has an ultrasonic probe attached thereto at the other end. Each of the six joints is provided with an angle detector to detect the angle of the joint. As a result, the ultrasonic probe can be arbitrarily positioned with an arbitrary beam direction. The positional information obtained from the angle detectors is used to provide the ultrasonic diagnostic apparatus with additional functions.

8 Claims, 4 Drawing Figures $QR = L_3 \sqrt{1 - \sin^2\theta_3 \sin^2\theta_\beta}$
$SR = L_3 \sin\theta_3 \cos\theta_\beta$
$ST = L_3 \sin\theta_3$
$PR = L_3 \sin\theta_3 \sin\theta_\beta$

ULTRASONIC DIAGNOSTIC PROBE SCANNER

BACKGROUND OF THE INVENTION

1. Field of the Invention

This invention relates to an ultrasonic diagnostic probe scanner by which an ultrasonic diagnostic probe can be arbitrarily positioned and arbitrarily oriented as to beam direction so as to make it possible to transmit an ultrasonic beam to a directed place in a desired direction.

2. Description of the Prior Art

In producing a tomogram of a specimen using an ultrasonic diagnostic apparatus, it is necessary to accurately position an ultrasonic probe with respect to the part of the specimen to be examined. This positioning involves both bringing the probe to the desired location in three-dimensional space and adjusting its angular orientation. In practical applications this is accomplished by means of an ultrasonic diagnostic probe scanner.

Conventional ultrasonic probe scanners consist of a scanner base which is placed in the vicinity of the body to be examined and a scanner system, one end of which is supported by the scanner base and the other end of which has the ultrasonic diagnostic probe attached thereto.

The operator of the ultrasonic diagnostic apparatus positions the ultrasonic diagnostic probe using the scanner system and then operates the ultrasonic diagnostic apparatus to display a tomogram of the specimen being examined.

However, the ultrasonic diagnostic probe scanner of prior art has drawbacks in that it cannot be accurately moved to and positioned at an arbitrary place opposing the specimen to be examined and cannot be accurately directed in any desired beam direction.

Furthermore, with the ultrasonic probe scanner according to prior art it has not been possible to obtain data signals representing the position and beam direction of a once-positioned ultrasonic diagnostic probe so as to be able to use these data signals in carrying out other functions, for example, the function of producing tomograms of the same cross section of the same specimen at different times.

SUMMARY OF THE INVENTION

Accordingly, it is the general object of the present invention to provide an ultrasonic diagnostic probe scanner which can accurately bring an ultrasonic diagnostic probe to an arbitrary selected position with an arbitrarily selected beam direction and which can supply signals representing said position and beam direction to an electronic processing unit.

In keeping with the principles of the present invention, this object is accomplished by producing an ultrasonic diagnostic probe scanner having a scanner system with six joints each of which can rotate within a predetermined plane, said scanner system being supported by a scanner base at one end and having an ultrasonic diagnostic probe attached on the other end, and six angle detectors associated one each with the six joints to detect their angles.

BRIEF DESCRIPTION OF THE DRAWINGS

The above mentioned features and object of the present invention will become more apparent from the following description in conjunction with the accompanying drawings, and in which.

DETAILED DESCRIPTION OF THE DRAWINGS

Figure 1:
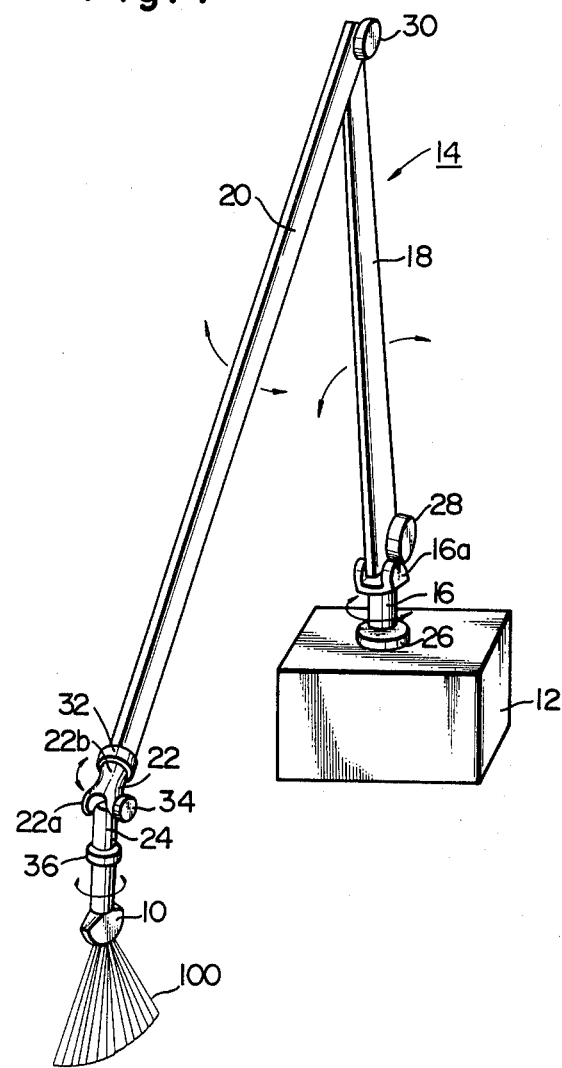
FIG. 1 is an illustration showing the construction of a preferred embodiment in accordance with the teachings of the present invention.

FIG. 1 shows a preferred embodiment in accordance with the teachings of the present invention. By the numeral 10 in the figure is indicated a sector scanning type ultrasonic probe, which after being brought into contact with a specimen to be examined (not shown) is driven by a diagnostic appratus (not shown) to transmit an ultrasonic beam 100, the echo signal of which is used by the diagnostic apparatus to produce a tomogram of the specimen.

The probe 10 is positioned by a scanner including a scanner base 12 which is placed in the vicinity of the specimen to be examined, and a scanner system 14 which is supported by the scanner base 12 at one end and has the probe 10 fixed on the other end.

The scanner system 14 has six joints, each of which can rotate within a predetermined plane, and six angle detectors attached to the joints.

A support 16 is rotatably mounted on the top of the scanner base 12, and a grip 16a fixed on the support 16 swingingly holds one end of an arm 18. On the other end of the arm 18 is swingingly supported one end of an arm 20, the other end of which holds a grip 22 which is rotatable with respect to the axis of the arm 20. On a gripping portion 22a of the grip 22 is pivoted a supporting rod 24 so as to be swingingable relative to the axis of a base portion 22b, and at the end of the supporting rod 24 is rotatably held the probe 10. As mentioned above, in the scanner according to this embodiment, the scanner system 14 has six joints each capable of rotating within a predetermined plane.

At the point of attachment of the support 16 on the scanner base 12 is provided an angle detector 26 which detects the angle of rotation of the support 16; at the point of attachment of the grip 16a to the arm 18, an angle detector 28 which detects the swinging angle of the arm 18; at the point of attachment of the arm 20 to the arm 18, an angle detector 30 which detects the swinging angle of the arm 20; at the point of attachment of the grip 22 to the arm 20, an angle detector 32 which detects the angle of rotation of the grip 22; at the point of attachment of the supporting rod 24 to the gripping portion 22a, an angle detector 34 which detects the swinging angle of the supporting rod 24; and at the top end of the supporting rod 24, an angle detector 36 which detects the angle of rotation of the probe 10. The signals from each of the angle detectors 26, 28, 30, 32, 34 and 36 are supplied to the diagnostic apparatus as information regarding the position of the probe 10 relative to the scanner base 12.

Figure 2:
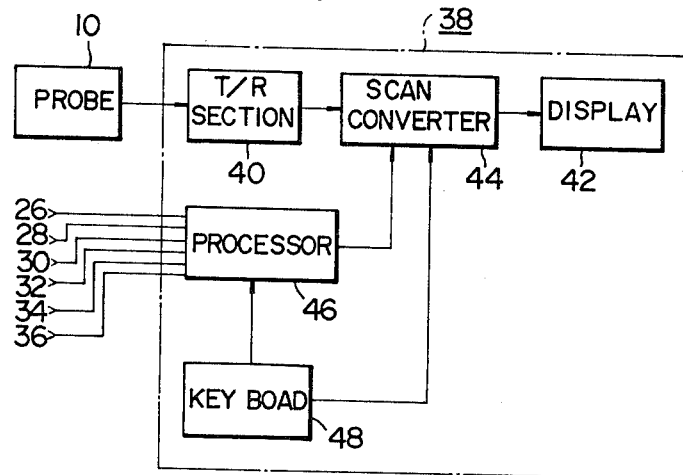
FIG. 2 is a block diagram of an ultrasonic diagnostic apparatus utilizing the embodiment shown in FIG. 1.

FIG. 2 shows a block diagram of the ultrasonic diagnostic apparatus utilizing the embodiment shown in FIG. 1. The diagnostic apparatus 38 includes a transmitting/receiving section 40 which transmits and controls the ultrasonic beam 100 of the probe 10 and detects the reflected echo signals from the probe 10, and a scan converter 44 which converts the signals detected by the transmitting/receiving section 40 to image signals suitable for use in scanning a display 42. The diagnostic apparatus 38 further has a processor 46 which processes the angle signals from the angle detectors 26, 28, 30, 32, 34 and 36 to obtain the position and beam direction of the probe 10 and outputs the processed results to the scan converter 44. Control signals from a keyboard 48 operated by an operator are supplied to the processor 46 and the scan converter 44. The processor 46 starts its processing operation upon receipt of the control signals. Upon receipt of the control signals from the keyboard 48, the scan converter 44 receives the processed results from the processor 46, and operates the display 42 to display both the position and beam direction of the probe 10 in the forms of characters, symbols or a graphic representation and the tomogram of the specimen under examination. The processor 46 has means for recording the processed results, i.e. data indicative of the position and beam direction of the probe 10, and the scan converter 44 can be operated to display the position and beam direction of the probe 10 on the display 42 by inputting the recorded data of the processor 46.

In the above description, each of the joints in the scanner system 14 can be fixed at an arbitrary angle, or can be released from such fixed state.

The construction of the preferred embodiment in accordance with the teachings of the present invention is as described in the foregoing. The operation of this scanner will now be described hereinafter.

The operator moves the probe 10 to a desired position on the specimen (i.e. a tissue) to be examined and fixes each of the joints so that the beam direction of the probe can be directed toward the specimen.

After the scanner has been set up in this manner, data from the angle detectors is fed to the processor 46 which processes this data to obtain and record the position and beam direction of the probe 10.

As mentioned above, since the scanner system 14 according to the present invention is provided with six joints, the position and the beam direction of the probe 10 can be freely and reliably adjusted with respect to the specimen to be examined.

In the following it will be explained how the scanner in accordance with the present invention can be used to obtain tomograms of the same cross section of the same specimen at different times.

The operator uses the keyboard 48 to read out the positional data and the beam direction data of the probe 10 in the preceding tomographic operation from the processor 46 and to feed this data to the scan converter 44. As a result, the position and beam direction of the probe 10 in the preceding tomographic operation is displayed on the display 42 in the form of charactors, symbols or graphic representation.

Next the operator moves the probe 10 to the position displayed by the ultrasonic diagnostic apparatus and fixes the probe 10 in the displayed beam direction. He then operates the ultrasonic diagnostic apparatus to produce a tomogram of the same cross section as that obtained in the preceding tomographic operation. As a result, any change in the conditions of the specimen under examination can be precisely judged.

As mentioned above, according to the embodiment the ultrasonic probe 10 can be moved to an arbitrary position and directed in an arbitrary beam direction. The positioning of the probe can thus be carried out with high accuracy.

In this embodiment, furthermore, once the position and beam direction of the ultrasonic probe 10 in a given tomographic operation are determined from the positional information from the angle detectors 26, 28, 30, 32, 34 and 36 by the processor 46 and the results of this determination are recorded therein, it is possible to produce a preceding tomogram of the same part of the specimen in a later tomographic operation, thus making it possible to accurately judge any change that has occurred in the specimen with time.

In this embodiment the scanner system 14 is equipped with six joints. As each of these joints is provided with one of the angle detectors 26, 28, 30, 32, 34 and 36, the processing operation of the processor 46 is simplified and the processing time thereof is reduced.

It is known that, from the point of cost, it is preferable to use a microcomputer as the processor 46. However, if the numbers of the joints in the scanner 14 is seven or more, the processor 46 will be required to perform processing of such complexity that, where a microcomputer is used, the processing time will be so long as to greatly impair the usefulness of the ultrasonic dianostic apparatus.

In view of this, the embodiment uses only six joints each equipped with an angle detector. In this way, the processing time of the processor is kept to a minimum.

The complicated process required to obtain the position of the probe 10 in the three-dimensional space has a much greater effect on the processing speed of the processor 46 than the process required to obtain the beam direction of the probe. In fact, the effect of the latter is so much smaller than that of the former as to be negligible.

Therefore, in the following only the processing equations for determining the position of the probe 10 in the three-dimensional space are discussed.

Figure 3:
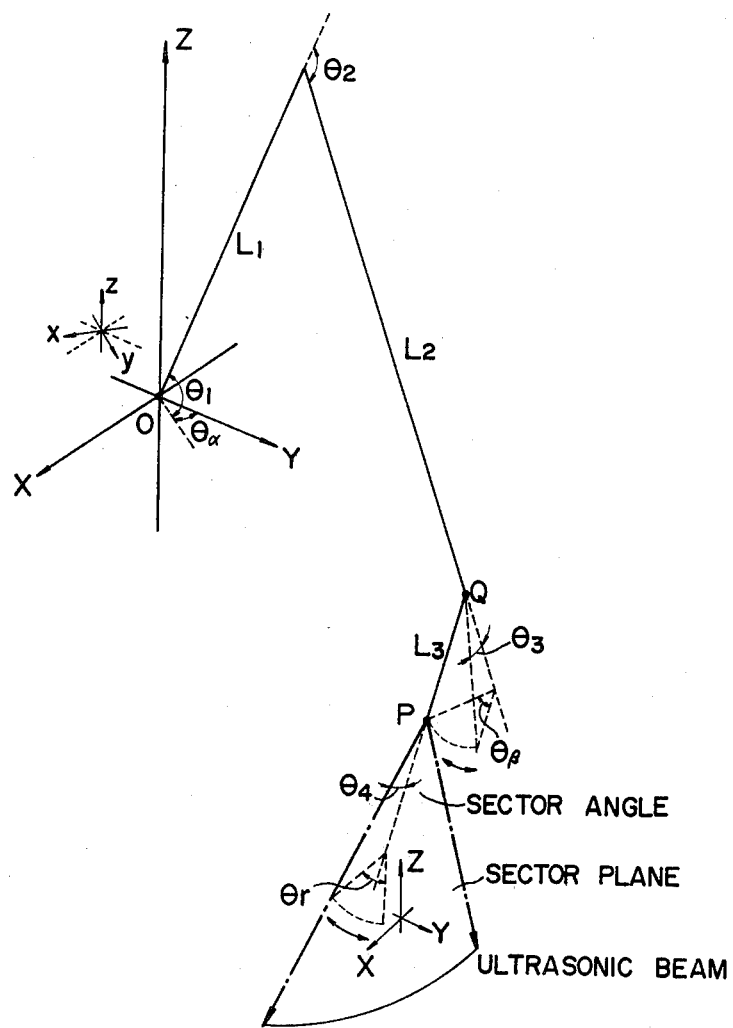

In FIG. 3, the magnitudes of the various members and angles of the scanner of the embodiment shown in FIG. 1 are denoted by symbols. Assume the origin of an X-Y-Z rectangular coordinate system to be located at the point of attachment of the arm 18 on the axis of rotation of the support 16.

Figure 4:
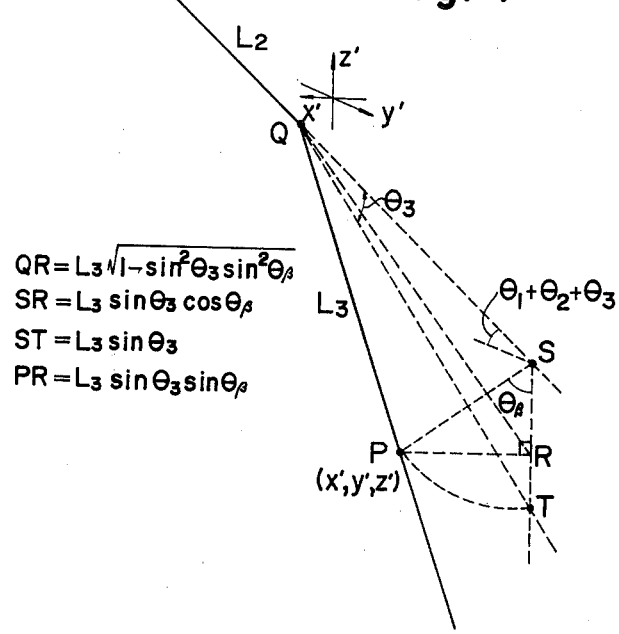
FIGS. 3 and 4 are illustrations for the purpose of describing how to calculate a position of the probe 10 shown in FIG. 1.

In FIG. 3, $\theta_\alpha$ denotes the angle detected by the angle detector 26; $\theta_1$, the angle detected by the angle detector 28; $\theta_2$, the angle detected by the angle detector 30; $\theta_3$, the angle detected by the angle detector 34; $\theta_\beta$, the angle detected by the angle detector 32; $\theta_\gamma$, the angle detected by the angle detector 36; and $\theta_4$, the sector angle of the probe 10. Also in FIG. 3, $L_1$ shows the distance from the joint of the arm 18 and the support 16 to the joint of the arm 18 and the arm 20; $L_2$, the distance from the joint of the arm 20 and the arm 18 to the joint of the grip 22 and the supporting rod 24; $L_3$, the distance from the joint of the grip 22 and the supporting rod 24 to the top end of the probe 10; and P, the top end of the probe 10. In FIG. 4, the joint portion of the grip 22 and the supporting rod 24 is shown in an enlarged view.

The magnitudes of $L_1$, $L_2$ and $L_3$ are supplied to the processor 46 in advance.

The coordinates of the top end P (Xp, Yp and Zp) can be represented by the following equations:

$$X_p = \tag{1}$$

-continued $$\sqrt{(L_3\sin\theta_3\sin\theta_\beta)^2 + \{L_3\sqrt{1-\sin^2\theta_3\sin^2\theta_\beta} \times \cos(\theta_1 + \theta_2 + \theta_3) + L_1\cos\theta_1 + L_2\cos(\theta_1 + \theta_2)\}^2} \times \sin\left(\theta_\alpha + \sin^{-1}\frac{L_3\sin\theta_3\sin\theta_\beta}{\sqrt{x^2 + y^2}}\right)$$

(2)

$$Y_p = \sqrt{(L_3\sin\theta_3\sin\theta_\beta)^2 + \{L_3\sqrt{1-\sin^2\theta_3\sin^2\theta_\beta} \times \cos(\theta_1 + \theta_2 + \theta_3) + L_1\cos\theta_1 + L_2\cos(\theta_1 + \theta_2)\}^2} \times$$

$$\cos\left\{\theta_\alpha + \cos^{-1}\frac{L_3\sqrt{1-\sin^2\theta_3\sin^2\theta_\beta} \times \cos(\theta_1 + \theta_2 + \theta_3) + L_1\cos\theta_1 + L_2\cos(\theta_1 + \theta_2)}{\sqrt{x^2 + y^2}}\right\}$$

(3)

$$Z_p = L_3\sqrt{1-\sin^2\theta_3\sin^2\theta_\beta} \times \sin(\theta_1 + \theta_2 + \theta_3) + L_1\sin\theta_1 + L_2\sin(\theta_1 + \theta_2)$$

In the processor 46 in FIG. 2, the position P of the probe 10 can be obtained by substituting the previously supplied values of $L_1$, $L_2$ and $L_3$ and the angles $\theta_\alpha$, $\theta_1$, $\theta_2$, $\theta_{62}$, and $\theta_3$ from the angle detectors 26, 28, 30, 32 and 34 into the above mentioned equations (1), (2) and (3).

The above mentioned equations (1), (2) and (3) will be explained hereinafter.

In FIG. 3, assume that X-Y-Z coordinate system is rotated by $\theta_\alpha$ in the X-Y plane and define this new coordinate system as the x-y-z coordinate system. In both of these coordinate systems the following equations hold:

$$X_p = \sqrt{x_p^2 + y_p^2} \times \sin\left(\theta_\alpha + \sin^{-1}\frac{x_p}{\sqrt{x_p^2 + y_p^2}}\right)$$

$$Y_p = \sqrt{x_p^2 + y_p^2} \times \cos\left(\theta_\alpha + \cos^{-1}\frac{y_p}{\sqrt{x_p^2 + y_p^2}}\right)$$

$$Z_p = z_p$$

First obtain the coordinates of the point P in the x-y-z coordinate system. In FIG. 4, let the intersection of $L_2$ and $L_3$ be point Q and define the coordinate system obtained by shifting the origin of the x-y-z coordinate point Q as the x'-y'-z' coordinate system. Then the coordinates ($x_p'$, $y_p'$, $z_p'$) of the point P are obtained as follows:

$$x'_p = L_3 \sin\theta_3 \times \sin\theta_\beta$$

$$y'_p = L_3\sqrt{1-\sin^2\theta_3\sin^2\theta_\beta} \times \cos(\theta_1 + \theta_2 + \theta_3)$$

$$z'_p = L_3\sqrt{1-\sin^2\theta_3\sin^2\theta_\beta} \times \sin(\theta_1 + \theta_2 + \theta_3)$$

From the above, the relation between $x_p$, $y_p$ and $z_p$ and $x_p'$, $y_p'$ and $z_p'$ is expressed as follows:

$$x_p = x_p'$$

$$y_p = y_p' + L_1\cos\theta_1 + L_2\cos(\theta_1 + \theta_2)$$

$$z_p = z_p' + L_1\sin\theta_1 + L_2\sin(\theta_1 + \theta_2)$$

Accordingly, the following equations hold:

$$x_p = L_3 \sin\theta_3 \times \sin\theta_\beta \tag{4}$$

$$y_p = L_3\sqrt{1-\sin^2\theta_3\sin^2\theta_\beta} \times \cos(\theta_1 + \theta_2 + \theta_3) + \tag{5}$$

$$L_1\cos\theta_1 + L_2\cos(\theta_1 + \theta_2)$$

$$z_p = L_3\sqrt{1-\sin^2\theta_3\sin^2\theta_\beta} \times \sin(\theta_1 + \theta_2 + \theta_3) + \tag{6}$$

$$L_1\sin\theta_1 + L_2\sin(\theta_1 + \theta_2)$$

When the equations (4), (5) and (6) are expressed in the X-Y-Z coordinate system, the previously mentioned equations (1), (2) and (3) are obtained.

Next, a case in which a compound scanning method is applied using the ultrasonic diagnostic probe scanner according to this embodiment will be described.

A compound scanning method can be generally defined as one in which the position and beam direction of the probe are varied in accordance with a combination of two or more simple scanning methods selected from among the linear, circular, arc, sector and other scanning methods. With compound scanning, it is possible to obtain high-quality tomographs.

In order to perform compound scanning using the embodiment shown in FIG. 1, three joints of the scanner system 14 are fixed so that scanning is carried out by a combination of mechanical scanning by the scanner system 14 and electronic sector scanning by the probe 10.

In FIG. 1, for example, when the support 16, the grip 22 and the probe 10 are fixed, the scanner system 14 can move the probe 10 in accordance with a predetermined straight locus and direct the probe 10 in an arbitrary selected direction. Accordingly, in this case, the mechanical linear scanning by the scanner system 14 and the electronic sector scanning of the probe 10 are combined to perform the compound sector scanning. While the compound scanning is being performed, the position P and beam direction of the probe 10 are processed by the processor 46 and the result is supplied to the scan converter 44. The scan converter 44 converts the wave signals detected by the transmitting/receiving section 40 and the processed result from the processor 46 into image signals. The display section 42 displays a broad, continuous sector scan tomogram along the compound scanning line, and, at the same time, the position and the beam direction of the probe can also be represented. Accordingly, the position of the probe in relation to the compound scan image can be seen on the screen of the display 42.

As is clear from the above description, according to the present invention, the probe can conveniently be positioned at an arbitrary selected place with an arbitrary selected beam direction.

According to the present invention, furthermore, once the probe has been positioned in the desired relationship to the specimen to be examined, data representing this position can be derived from the scanner and used to provide the ultrasonic diagnostic apparatus in which the scanner is employed with additional functions.

What we claim is:

1. An ultrasonic diagnostic probe scanner comprising:

a base;

a support rotatably coupled to said base such that said support is perpendicular to said base and rotates about an axis perpendicular to said base;

a first sensor for sensing an angle of rotation of said support;

a first arm swingably coupled to said support such that it swings relative to said support;

a second sensor for sensing an angle of swing of said first arm relative to said support;

a second arm swingably coupled to said first arm such that it swings relative to said first arm;

a third sensor for sensing an angle of swing of said second arm relative to said first arm;

a grip rotatably coupled to said second arm such that it rotates about a longitudinal axis of said second arm;

a fourth sensor for sensing an angle of rotation of said grip relative to said second arm;

a first support rod swingably coupled to said grip such that it swings relative to said grip;

a fifth sensor for sensing an angle of swing of said first support rod relative to said grip;

a second support rod rotatably coupled to said first support rod such that it rotates about a longitudinal axis of said first support rod;

a sixth sensor for sensing an angle of rotation of said second support rod relative to said first support rod; and an ultrasonic probe coupled to an end of said second support rod;

whereby outputs of said first, second, third, fourth, fifth and sixth sensors accurately and repeatably set a position of said probe.

2. An ultrasonic diagnostic probe scanner according to claim 1 further comprising a processor means for receiving and processing a detected angle from said six angle detectors to obtain a position and beam direction of a probe of said ultrasonic diagnostic probe scanner.

3. An ultrasonic diagnostic probe scanner according to claim 2 further comprising a display means coupled to said processor means for displaying said position and beam direction of said probe.

4. An ultrasonic diagnostic probe scanner according to claim 3 wherein said processor means further comprises a recording means for recording said position and beam direction.

5. An ultrasonic diagnostic probe scanner according to claim 4 wherein said processor means comprises a microprocessor.

6. An ultrasonic diagnostic probe scanner according to claim 4 wherein said processor means and said display means are provided within said scanner base.

7. An ultrasonic diagnostic probe scanner according to claim 4 further comprising a manual data entry means coupled to said processor means for causing said display means to display a preceding position and beam direction recorded in said processor means.

8. An ultrasonic diagnostic probe scanner means according to claim 7 wherein said manual data entry means comprises a keyboard.

* * * * *